United States Patent [19]
Tachi et al.

[11] Patent Number: 6,063,619
[45] Date of Patent: May 16, 2000

[54] ANAEROBIC INCUBATOR

[75] Inventors: Hiromi Tachi; Hisanori Fukushima, both of Osaka, Japan

[73] Assignee: Hisanori Fukushima, Osaka, Japan

[21] Appl. No.: 09/124,551

[22] Filed: Jul. 28, 1998

[51] Int. Cl.[7] .................................................. C12M 1/00
[52] U.S. Cl. ..................................... 435/303.2; 435/304.1; 435/809
[58] Field of Search .............................. 435/303.2, 304.1, 435/288.1, 809; 219/438, 439, 441, 442; 422/104

[56] References Cited

U.S. PATENT DOCUMENTS 3,562,114  2/1971  Steidl et al. .
4,188,265  2/1980  Larro .
4,307,287  12/1981  Weiss .
5,345,063  9/1994  Reusche et al. .

*Primary Examiner*—William H. Beisner
*Attorney, Agent, or Firm*—Vedder Price Kaufman & Kammholz

[57] ABSTRACT

An anaerobic incubator providing for a consistently anaerobic and constant-temperature environment within an incubation jar for culture of root canal contents which comprises an incubator body, an open-top incubation jar disposed in said incubator body and comprising an outer cylindrical casing made of aluminum and, as fitted intimately therein, an inner cylindrical casing made of stainless steel, a planar heater disposed in intimate contact with the exterior surface of said outer cylindrical casing, and a temperature sensor mounted in the wall of said outer cylindrical casing. The anaerobic incubator of the invention does not require a time-consuming procedure particularly for changing water, is free from aging of heater and temperature sensor performances, and provides for improved responsiveness and controllability of the incubation jar.

1 Claim, 3 Drawing Sheets

ANAEROBIC INCUBATOR

FIELD OF THE INVENTION

The present invention relates to an anaerobic incubator which is primarily used in dental clinics for culture of root canal contents.

DESCRIPTION OF THE RELATED ART

While, in dental practice, root canal contents are cultured under anaerobic conditions for determining whether the case is ripe for root canal filling, the conventional anaerobic jar used for the purpose comprises an outer cylindrical casing and an inner cylindrical casing with water filled in the space between the casings. The interior of the jar is secluded in an anaerobic state and the interposed water is heated with a submerged heater to maintain the interior of the jar at a constant temperature.

However, since this type of anaerobic jar is used with water filled between its outer and inner casings as mentioned above, the water must be replaced with fresh one after each cultural session but the procedure is time-consuming and troublesome. Therefore, after using the jar it is common practice to leave it filled with water without draining till the next cultural session but the practice encourages proliferation of adventitious microorganisms. Furthermore, since the necessary heater and temperature sensor are disposed in the body of said water, scales and rust tend to form on the heater and sensor surfaces so that both heating efficiency and sensor sensitivity are adversely affected as the jar is repeatedly used.

Moreover, should an anaerobic jar of this type be provided with a rack means by which a plurality of culture dishes might be conveniently supported in tiers, the utility of the incubator would be greatly increased. In addition, the responsiveness and controllability of the incubator should also be improved if the heat conduction medium used should have an improved heat conductivity.

Having been developed in view of the above state of the art, the present invention has for its object to provide an anaerobic incubator which does not require a troublesome procedure inclusive of water change and is free from aging of heater and sensor performances and superior in responsiveness and controllability.

SUMMARY OF THE INVENTION

Designed to accomplish the above object, the anaerobic incubator of the present invention comprises an incubation jar for establishing anaerobic conditions and maintaining a constant temperature necessary for culture of root canal contents, said incubation jar having a top opening and comprising an aluminum outer cylindrical casing, a stainless steel inner cylindrical casing fitted in said outer cylindrical casing in close contact therewith, a planar heater installed in intimate contact with the exterior surface of said outer casing, and a temperature sensor mounted in the wall of said outer casing.

In the above construction, as the planar heater is actuated, the exterior surface of the outer casing of the jar is heated. Since the outer casing made of aluminum has a high thermal conductivity, the whole body of the outer casing is rapidly heated to the necessary temperature. Moreover, since the inner casing is disposed in intimate contact with the outer casing, the inner casing is also rapidly heated so that the interior of the incubator is heated almost immediately.

On the other hand, since a temperature sensor is installed within the wall of the outer casing, the temperature of the outer casing can be accurately detected, and after the interior of the jar has been heated to a predetermined temperature, this temperature is accurately maintained in response to the output of said temperature sensor.

Since, in the present invention, the inner cylindrical casing is fitted in the outer cylindrical casing in intimate contact therewith and the planar heater is installed in intimate contact with the exterior surface of the outer casing, the time-consuming and troublesome procedure particularly for changing water is not required at all. Moreover, since water is not used in the present invention, there is no fear of scale formation on the heater and sensor to detract from their performances.

Furthermore, since both the outer and inner cylindrical casings are made of metallic materials having high heat conductivity, the responsiveness of the system is very satisfactory so that a constant temperature can be consistently maintained. The reaction of oxygen with hydrogen, which is necessary to render the interior of the incubation jar anaerobic, gives rise to water but since the inner casing is made of stainless steel, there is no fear of rust formation.

Another embodiment of the invention is an anaerobic incubator which is further provided with a dish rack capable of supporting a plurality of culture dishes. This dish rack has upright segments adapted to engage each culture dish at either sides thereof, said upright segments having been formed by bending a stainless steel wire each in the configuration of an inverted U letter in front view. Provided between said dish rack as installed and said inner casing is a free space for accommodating the so-called gas pak.

The above anaerobic incubator is used in the following manner. The root canal contents to be tested are smeared or streaked onto a culture medium in the culture dish and a plurality of disks coated with various antibiotics are placed on the medium. The dishes are then mounted in the dish rack. Since the upright segments of the dish rack are formed by bending a stainless steel wire each in an inverted U configuration in front view as described above and the right and left edges of the dish are respectively engaged by the two lengths of the wire, the dish can be supported securely in a horizontal position. When a plurality of dishes are to be tested, they can be set on the rack one after another in tiers.

After the culture dish or dishes are thus mounted in the rack, the rack is set in the incubator. Since the upright segments of the rack are formed of a wire bent each in an inverted U configuration in front view, the rack can be securely set in position by utilizing the top loop of the inverted U-shaped structure. After closure of the incubation jar, the interior of the jar must be made anaerobic. For this purpose, it is common practice to employ the so-called gas pak which generates hydrogen and carbon dioxide gases in the presence of water to create the optimum anaerobic environment for isolation of anaerobic microorganisms. The gas pak mentioned above is set in the free space between the dish rack and the inner cylindrical casing. Since the rack is made of a wire material, the evolved hydrogen gas is allowed to diffuse rapidly within the jar to react with oxygen. Since the rack is made of stainless steel, it is resistant to rusting by byproduct water.

DETAILED DESCRIPTION OF THE PREFERRED EMBODIMENTS

The anaerobic incubator 1 of the invention is now described in further detail.

Figure 1:
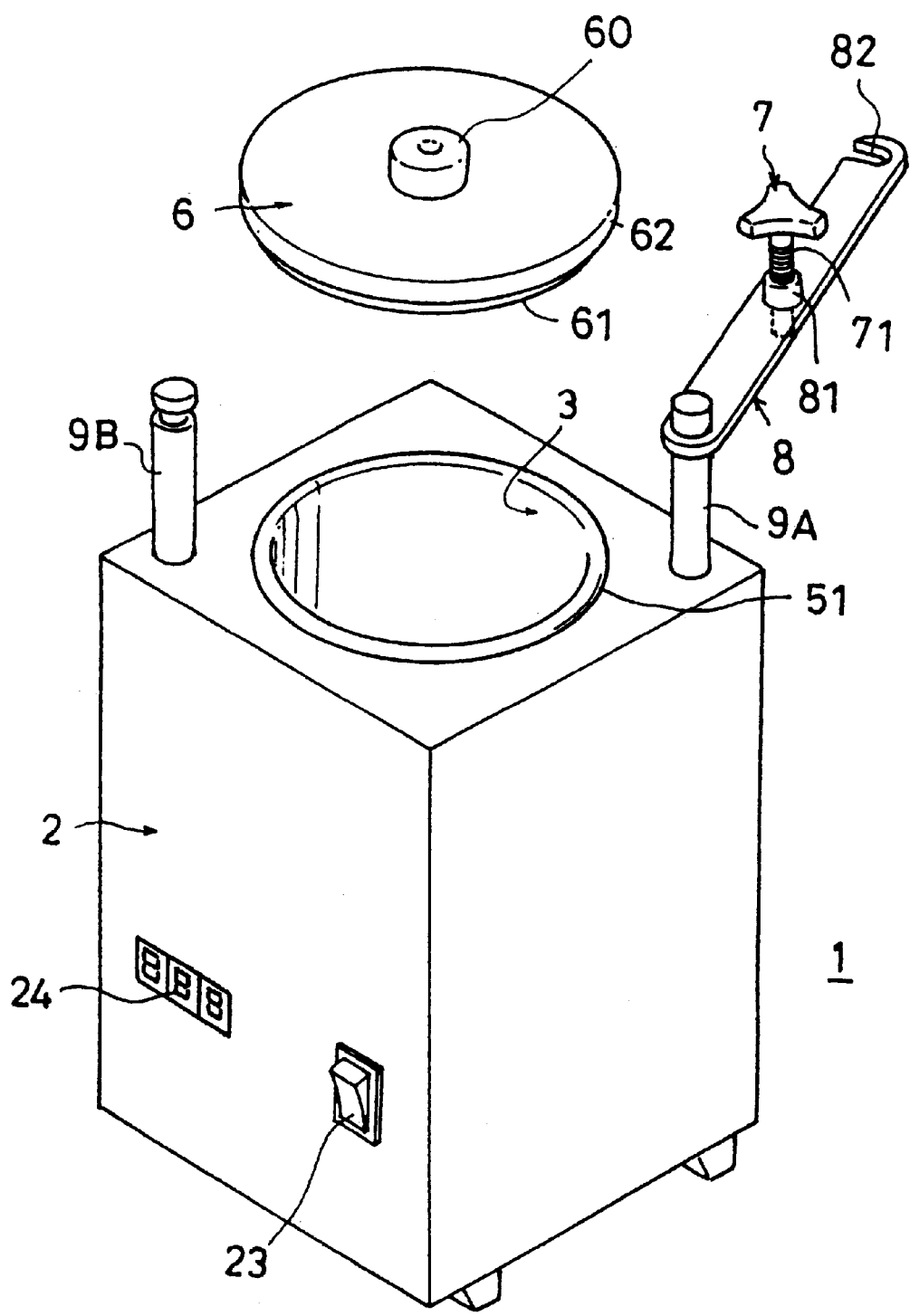
FIG. 1 is a disassembled perspective view showing an anaerobic incubator embodying the principles of the invention.
Figure 2:
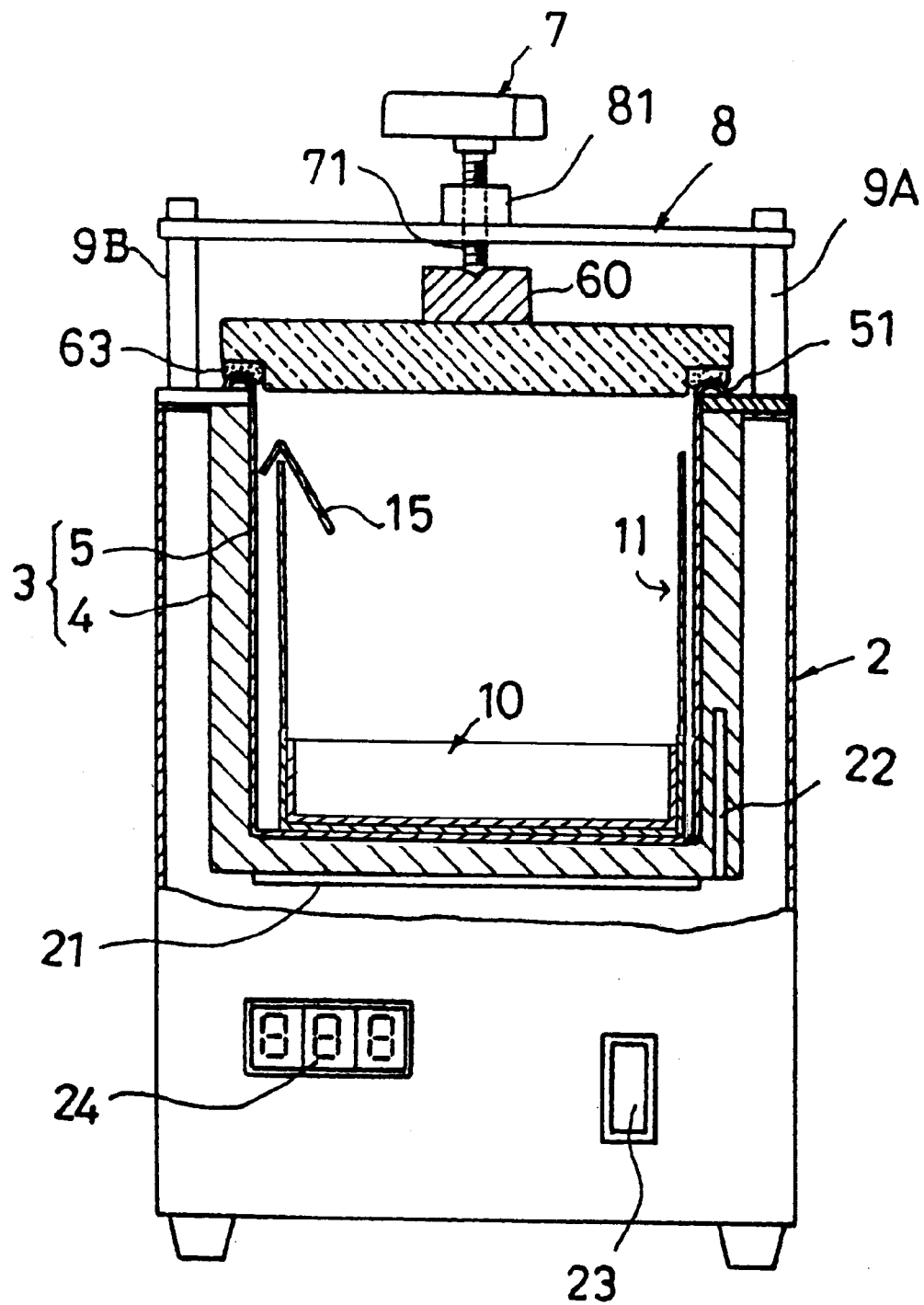
FIG. 2 is a longitudinal section view of the anaerobic incubator of FIG. 1 in use.

FIG. 1 is a disassembled perspective view showing an anaerobic incubator of the invention and FIG. 2 is a longitudinal section view thereof in use.

The anaerobic incubator 1 of the present invention comprises a box-shaped incubator body 2, an incubation jar 3 with a top opening, and a gas-tight cover 6 adapted to close off said top opening hermetically. The incubation jar 3 is formed in the shape of a bottomed cylinder which is open exclusively at its top and comprises an aluminum outer casing 4 and a stainless steel inner casing 5 fitted intimately within said outer casing. The inner casing 5 is relatively reduced in wall thickness with respect to the outer casing 4, with its top end portion being bent radially outward in a generally semicircular fashion to form a flange 51.

The incubator body 2 is equipped with a rubber heater 21 comprising a planar heater wire covered with rubber in the position corresponding to the bottom of the incubation jar 3 so that the incubation jar 3 is efficiently heated by said rubber heater 21. Furthermore, in a part of the peripheral wall of the outer casing 4, there is provided a temperature sensor 22 as inserted in an upright position from its bottom end so that the caloric output of the rubber heater 21 may be varied according to the output of this temperature sensor 22. Thus, by the heater 21 and temperature sensor 22, the incubation jar 3 is maintained at a constant temperature. The temperature of the incubation jar 3 is set to 37° C. which is substantially equal to the human body temperature and best suited to culture of most anaerobic microorganisms.

The heating of the incubation jar by the rubber heater 21 is controlled with a switch 23 provided on the front of the incubator body 2 and the temperature detected by the temperature sensor 22 is displayed in a digital format on a display 24 which is also mounted on the front of the incubator body 2.

The gas-tight cover 6 is a disk-shaped element having a columnar projection 60. The disk-shaped element is formed as a stepped disk, with its small-diameter annular portion 61 having a diameter slightly smaller than the diameter of the body of said inner cylindrical casing 5 and its large-diameter portion 62 having a diameter approximately equal to the outer diameter of the flange 51 of said inner casing 5. Furthermore, an annular silicone rubber sheet 63 is secured in position beneath the whole stepped area surrounding the small-diameter portion of the gas-tight cover 6. The gas-tight cover 6 is preferably made of clear acrylic material.

The gas-tight cover 6 is installed in position by inserting its small-diameter portion 61 into the inner cylindrical casing 5 and, with the silicone rubber sheet 63 abutted against the flange 51 of said inner casing 5, fastened with a fastener 7 so as to close off the inner casing 5 gas-tight.

The fastener 7 is threadedly connected to an elongated bridging member 8 in its center 81 in such a manner that its screw shaft 71 may be advanced or retreated according to the turning direction of the fastener 7. The bridging member 8 is rotable in a horizontal plane about a pivot shaft 9A and has a free end 82 which is recessed so as to be engagieable with an engaging shaft 9B. In this construction, the bridging member 8 can be locked by rotating it until its free end 82 has been engaged by the engaging shaft 10.

Thus, after closure of the top opening of the incubation jar 3 of the incubator body 2 with said gas-tight cover 6, the free end 82 of the bridging member 8 is brought into engagement with said engaging shaft 10. Thereafter, as the fastener 7 is turned to advance the screw shaft 71 in a downward direction, the screw shaft 71 presses down the projection 60 of the gas-tight cover 6. Thereupon, the silicone rubber sheet 63 attached to the underside of the large-diameter portion 62 of the gas-tight cover 6 is pressed against the flange 51 of the inner casing 5 to hermetically seal off the inner casing.

Figure 3A:
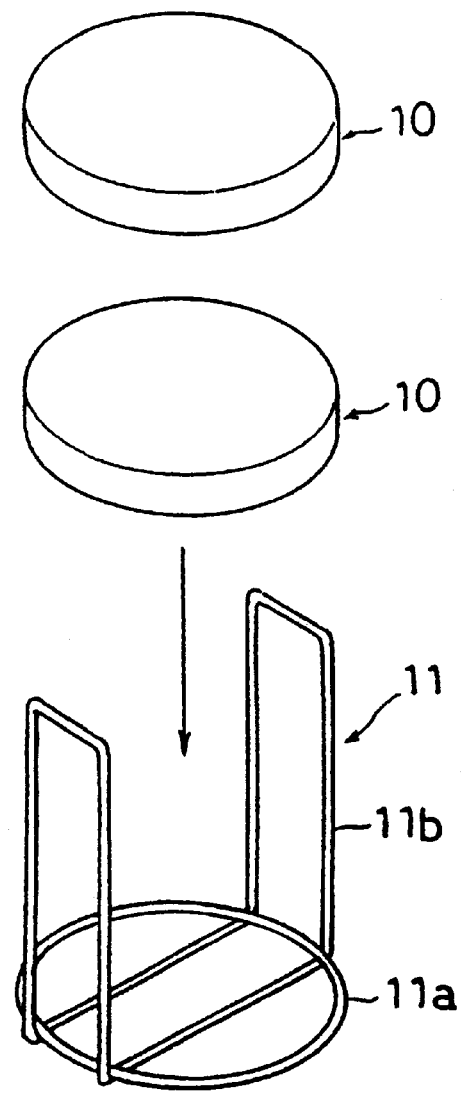
FIGS. 3(a) and 3(b) are perspective view showing culture dishes and a dish rack to be set in the anaerobic incubator of the invention.
Figure 3B:
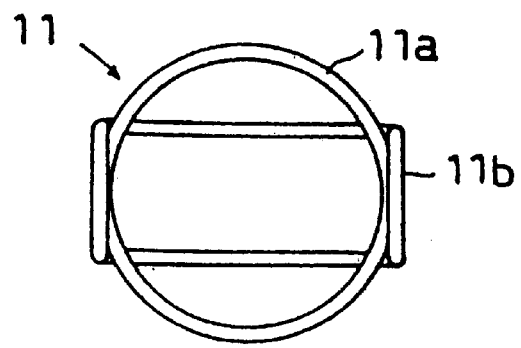

Referring to FIG. 3(a), a culture dish 10 is mounted on a rack 11 and set in the incubation jar 3 of the incubator body 2.

The rack 11 comprises a ring-shaped segment 11a formed by bending a stainless steel wire into a circular configuration and, as rigidly secured thereto, generally rectangular segments 11b formed by bending a similar stainless steel wire in the shape of a bracket. The rectangular segments 11b can be fabricated by forming a wire into an elongated rectangular configuration and bending it into a generally bracket-shaped element. Thus, each of said upright segments (11b) assumes the form of an inverted letter U in front view, with two lengths of the wire available for engagement with the culture dish on either side thereof. Therefore, despite its simple and lightweight construction, the rack 11 is capable of holding a plurality of dishes in horizontal tiers with sufficient stability. In the state in which the dish rack 11 has been installed in the incubation jar 3, there is a free space for accommodating the so-called gas pak, which is to be described hereinafter, between the rack 11 and the inner casing 5.

The manner in which the anaerobic incubator 1 of the invention is used is now described.

First, the root canal contents to be tested are smeared onto a culture medium in dish 10 and a plurality of sensitivity assay disks (about 3~4 mm in diameter) coated with various antibiotics are placed on the medium. Then, the dish is mounted on the dish rack 11. When a plurality of samples is to be tested, a plurality of dishes 10 . . . are serially set in tiers on the rack 11.

Meanwhile, as the switch 23 is turned on, the incubation jar 3 is preheated to 37° C. by the rubber heater 21. The dish rack 11 carrying said plurality of dishes 10 . . . is held by hand at its top and installed in the preheated incubation jar 3.

Then, the interior of the incubation jar 3 is made anaerobic. A specific procedure comprises filling said gas pak with about 10 ml of water, setting the water-filled gas pak into the free space between the dish rack 11 and the inner casing 5, and closing up the incubation jar 3 hermetically with the gas-tight cover 6 by operating said fastener 7. Thereupon, the hydrogen liberated by the reaction of water with sodium borate reacts with oxygen in the incubation jar 3 to yield water, while the reaction between sodium carbonate and citric acid establishes a carbon dioxide concentration of about 8%. Thus, by adding about 10 ml of water to the gas pak to let it react with the reagents contained in the gas pak, an anaerobic environment optimal for isolation of anaerobic microorganisms can be successfully established. When an indicator 15 is placed in the incubation jar 3 beforehand, a charge in color, from blue to white, for instance, occurs in about 5 hours, indicating that the interior of the jar has been rendered anaerobic.

After a predetermined time, for example 48 hours, of standing, the dish 10 is taken out and checked for the change in the medium. Assuming that an initially red medium is used, the antibiotic applied to the sensitivity assay disk is considered effective when the medium around the disk remains red and, therefore, this result can be exploited in dental therapy.

With the incubation jar comprising an aluminum outer casing and a stainless steel inner casing fitted intimately into the outer casing, the anaerobic incubator of the invention, unlike the conventional jar, can be put to use without the need to supply water to the clearance between casings. This means that it is unnecessary to change water and that there is no fear of proliferation of adventitious bacteria or formation of scales and rust. Furthermore, since the incubation jar is made of metal, a high heat conductivity is assured and the interior of the incubation jar can be maintained at a predetermined temperature with high efficiency and little variation.

In addition, the anaerobic incubator of the invention provides for chair-side anaerobic culture and, therefore, is of great use to dentists. The related dental practice is now described in detail.

Pulpitis and apical periodontitis, secondary to caries, are infectious diseases associated with the bacterial flora in the oral cavity. The current therapy of pulpitis comprises removing the pulp under local anesthesia, enlarging the root canal with a reamer or a file, applying an antiseptic solution into the root canal, and on disappearance of symptoms, filling the canal with gutta-percha point to complete the treatment. This therapeutic course includes a procedure for eliminating bacteria from the root canal but it is usually not confirmed whether the bacteria have been successfully eliminated or not.

According to Ikenaga et al., the pulp was infected in more than 90% of patients with pulpitis complaining of thermal pain or spontaneous pain, and even immediately prior to root canal filling after treatment, bacteria were detected in more than 30% of cases according to the report of Yoshida et al. and more than 25% according to the report of Tokunaga et al. This is why retreatment is required after root canal filling.

However, when the anaerobic incubator of the invention is used before root canal filling, it is possible to diagnose whether further treatment is necessary or not prior to the next examination day. Moreover, by using a blood agar medium for anaerobic bacteria in the practice of the invention, both the taxon and population of bacteria can be established so that the dynamic response of bacteria to therapy can be monitored. Furthermore, by carrying out aerobic culture following anaerobic culture with the incubator of the invention, not only the presence of anaerobic bacteria but also the involvement of aerobic microorganisms such as candial species can be demonstrated. Candial species are frequently isolated from the root canal but are hard to be eradicated. However, since those microorganisms can be easily detected in accordance with the invention, they can be expediently eliminated by topical administration of amphotericin B.

While the current therapeutic modality for apical lesions is not much different from that for pulpitis, a bacteriological examination of root canal contents can be indicated. However, since the conventional sterility test involves use of a liquid medium or a semi-fluid medium, the quantitative and qualitative determination of the bacteria are not feasible unlike in the present invention. Moreover, in patients presenting with acute symptoms such as cellulitis, the susceptibility of the associated bacteria to antibiotics can be tested to select an antibiotic of first choice and the particular antibiotic be topically administered.

Disappearance of clinical symptoms does not necessarily mean a complete cure. According to Tokunaga, the positive rate before root canal filling (after disappearance of clinical symptoms) is higher with a greater viable count in root canal infections than in pulpitis. Therefore, in root canal infections, a sterility test prior to root canal filling is more important.

Thus, an examination system using the anaerobic incubator of the invention is not only useful for diagnosis but highly meritorious in that an exact therapeutic guideline can be established.

What is claimed is:

1. An anaerobic incubator comprising an incubator body, an incubation jar with a top opening integrated with said incubator body and a gas-tight cover for closing off said top opening hermetically in which:

said incubator body has on its upper surface a pivot shaft and an engaging shaft, a bridging member rotatable in a horizontal plane about said pivot shaft has its end recessed so as to be engageable with said engaging shaft, a fastener is threadedly connected to the center of said bridging member so that a screw shaft may be advanced or retreated according to the turning of said fastener, said gas-tight cover has a columnar projection corresponding to the position of said screw shaft so as to be pressed down by said screw shaft, said incubation jar has an outer cylindrical casing made of aluminum fitted intimately in an inner cylindrical casing made of stainless steel, said outer cylindrical casing has a planar heater in intimate contact with its exterior surface and a temperature sensor in its wall, a dish rack capable of supporting a plurality of culture dishes in tiers has upright segments for engaging both lateral sides of each culture dish and supporting it in a horizontal position, said upright segments are formed by bending a stainless steel wire in an inverted letter U shape in front view, a free space is provided for accommodating a gas pak between said dish rack and said inner cylindrical casing, said gas pak has components which generate hydrogen and carbon dioxide gases in the presence of water and an anaerobic environment is created only by putting water in said gas pak, and chair-side anaerobic culture is thus made possible.

\* \* \* \* \*